(12) United States Patent
Pratx et al.

(10) Patent No.: US 8,314,796 B2
(45) Date of Patent: Nov. 20, 2012

(54) METHOD OF RECONSTRUCTING A TOMOGRAPHIC IMAGE USING A GRAPHICS PROCESSING UNIT

(75) Inventors: Guillem Pratx, Stanford, CA (US); Peter D. Olcott, Menlo Park, CA (US); Craig S. Levin, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1166 days.

(21) Appl. No.: 11/710,273

(22) Filed: Feb. 23, 2007

(65) Prior Publication Data
US 2007/0201611 A1 Aug. 30, 2007

Related U.S. Application Data

(60) Provisional application No. 60/776,263, filed on Feb. 24, 2006.

(51) Int. Cl.
*G06T 17/00* (2006.01)
*G06K 9/00* (2006.01)
(52) U.S. Cl. ............. 345/424; 345/419; 382/131; 378/4
(58) Field of Classification Search .................. 382/131; 345/419, 424; 378/4
See application file for complete search history.

(56) References Cited

U.S. PATENT DOCUMENTS

| 6,381,349 B1* | 4/2002 | Zeng et al. ..................... 382/128 |
| 7,365,335 B2* | 4/2008 | Gagnon et al. ............ 250/363.04 |
| 2007/0040122 A1* | 2/2007 | Manjeshwar et al. ... 250/363.03 |
| 2007/0177713 A1* | 8/2007 | Kohler et al. ..................... 378/4 |

OTHER PUBLICATIONS

Xu, Fang, and Klaus Mueller. "Accelerating Popular Tomographic Reconstruction Algorithms on Commodity PC Graphics Hardware." IEEE Transactions on Nuclear Science52.3 (Jun. 2005).*
Chidlow, Ken, and Torsten Moller. "Rapid Emission Tomography Reconstruction." Volume Graphics (2003): 1-12.*
Rahmim, Arman, Ju-Chieh Cheng, Stephan Blinder, Maurie-Laure Camborde, and Vesna Sossi. "Statistical Dynamic Image Reconstruction in State-of-the-art High-resolution PET." Physics in Medicine and Biology 50.20 (2005): 4887-912.*
Beenhouwer et al., "Graphics Hardware Accelerated Reconstruction of SPECT with a slat collimated strip detector", 2006 World Congress in Computer Science, Computer Engineering and Applied Computing.

* cited by examiner

*Primary Examiner* — Xiao M. Wu
*Assistant Examiner* — Scott E Sonners
(74) *Attorney, Agent, or Firm* — Koppel, Patrick, Heybl & Philpott; Michael J. Ram

(57) ABSTRACT

The present invention provides a method of reconstructing a tomographic image. In a first step, a tomographic image is forward-projected along a list of geometrical lines in a GPU. This list of geometrical lines may be list-mode event data acquired from a tomographic scanner. Alternatively, the list may be a list of weighted lines derived from a sinogram, a histogram, or a timogram acquired from a tomographic scanner. Next, the list of geometrical lines is back-projected into a 3-dimensional volume using the GPU. The results of the forward- and back-projection are then used to reconstruct the tomographic image, which is then provided as an output, e.g. to make the image available for further processing. Examples of output include storage on a storage medium and display on a display device.

20 Claims, 6 Drawing Sheets

(b)

(a)

METHOD OF RECONSTRUCTING A TOMOGRAPHIC IMAGE USING A GRAPHICS PROCESSING UNIT

CROSS-REFERENCE TO RELATED APPLICATIONS

This application claims priority from U.S. Provisional Patent Application No. 60/776,263, filed Feb. 24, 2006, which is incorporated herein by reference.

FEDERALLY-SPONSORED RESEARCH OR DEVELOPMENT

This invention was made with Government support under contracts EB003283 and CA098691 awarded by the National Institutes of Health. The Government has certain rights in this invention.

FIELD OF THE INVENTION

The present invention relates generally to medical image reconstruction. More particularly, the present invention relates to methods of reconstructing a tomographic image using a graphics processing unit (GPU).

BACKGROUND

Tomographic image reconstruction is usually performed on a computer central processing unit (CPU). CPU's are suitable for general purpose computation. For this reason, they are easy to use and program. However, list-mode tomographic image reconstruction on CPUs is computationally intensive, due to the large number of line back- and forward-projections that need to be performed.

The number of detector elements in tomographic imaging systems continues to increase in order to improve resolution and sensitivity. One major consequence of this is that sinogram-based image reconstruction iterative algorithms have become less attractive due to large memory requirements for storing the system matrix. On-the-fly list-mode based iterative reconstruction schemes circumvent the memory issue but are computationally expensive. For example, in list-mode 3D-Ordered Subsets Expectation Maximization (OSEM), a very large number (typically $>10^8$) of forward projections from the image voxel space onto lines of response (response lines between any two system detector elements) are performed. A similar number of back projections are done from the lines of response onto the voxel space. When reconstruction is performed on CPUs, most of the computation time is spent doing these operations. One expensive solution to this problem is to use a large cluster of computers to perform 3D list-mode reconstruction. Without such a computer cluster, practical reconstruction for most applications is limited to Filtered Back projection (FBP) or rebinned 3D data for 2D-OSEM.

Graphics cards are usually used to render 3-dimensional geometries on a computer screen (for example, in video games). The main microprocessor of a graphics card is called a graphics processing unit (GPU). The gaming and computer graphics rendering industries have created a market for powerful and cost-effective GPU chips. GPU performances are currently doubling every six months. GPU raw performance can now outperform CPU performance, but because of their architecture, it is very difficult to use GPUs in place of CPUs.

Recently, advances have been made in using GPUs for scientific computing applications such as tomographic image reconstruction. Current GPU implementations use only the 2D texture-mapping capability of the GPU and have been limited to fan-beam and parallel beam X-ray computed tomography (X-Ray CT) image reconstruction. These implementations cannot accomplish the individual line forward- and back-projection used in computationally expensive list-mode reconstruction schemes. In addition, these methods do not allow incorporating a blurring kernel to each line. Accordingly, there is a need in the art to develop methods of implementing tomographic line projection algorithms on GPUs.

SUMMARY OF THE INVENTION

The present invention provides a method of reconstructing a tomographic image. In a first step, a tomographic image is forward-projected along a list of geometrical lines in a GPU. This list of geometrical lines may be list-mode event data acquired from a tomographic scanner. Preferably, the list-mode event data contains time-of-flight information or temporal information. Alternatively, the list may be a list of weighted lines derived from a sinogram, a histogram, or a timogram acquired from a tomographic scanner. According to the present invention, the data may be acquired by any type of tomographic scanner, including but not limited to a positron emission tomography (PET) scanner, a single photon emission computed tomography (SPECT) scanner, or an X-ray computed tomography (CT) scanner. Next, the list of geometrical lines is back-projected into a 3-dimensional volume using the GPU. The results of the forward- and back-projection are then used to reconstruct the tomographic image, which is then provided as an output, e.g. to make the image available for further processing. Examples of output include storage on a storage medium and display on a display device. Any display may be used according to the present invention, including but not limited to a handheld device, a portable computer, or a computer monitor.

In a preferred embodiment, the forward-projecting and/or the back-projecting is implemented using a parametric 3-dimensional blurring kernel. In one embodiment, the blurring kernel is a 2-dimensional Gaussian perpendicular to each of the lines. In another embodiment, the blurring kernel is a 1-dimensional time of flight blurring kernel. In yet another embodiment, parametric 3-dimensional blurring kernel uses trilinear interpolation.

Also preferably, the GPU is initialized prior to implementing the method of the present invention. Initializing preferably includes setting projection to be orthographic, activating blending, and setting the target of rastering to be a 2-dimensional texture map.

According to the present invention, the forward-projection preferably includes the following steps. First, a 3-dimensional voxel array is inputted into the GPU. In addition, the list of geometrical lines is inputted into the GPU, where the list of geometrical lines is defined within the 3-dimensional voxel array. Weighted samples values are then determined by sampling the 3-dimensional voxel array at several locations along each of the geometrical lines in the GPU. Preferably, the values are determined using shaders in the GPU. Next, the weighted samples values of the voxels along each of the geometrical lines are recorded into GPU memory. Preferably, the recording is accomplished using texture mapping of the weighted samples onto sequential parallel lines. Finally, a sum of the weighted samples values for each of the geometrical lines is calculated in the GPU memory. Preferably, the sum is calculated using shaders in the GPU.

Back-projecting according to the present invention also preferably includes a number of steps. In one embodiment, the list of geometrical lines is first inputted into the GPU. Next, slices are defined in a 3-dimensional volume, where the 3-dimensional volume includes the geometrical lines. Preferably, the slices are defined using a cutting planes operation on the GPU. More preferably, the cutting planes are set to include 4 slices, where color is used to encode slice depth. A 2-dimensional texture of each of the slices is then defined by projecting and rastering the portion of the geometrical lines that is contained within each of the slices into a set of weighted pixels. Preferably, projecting is accomplished using shaders in the GPU. Each of these 2-dimensional textures is then inserted into a 3-dimensional voxel array stored on the GPU.

In an alternative embodiment, back-projection includes the following list of steps. First, the list of geometrical lines is inputted into the GPU. Next, the geometrical lines are weighted using a 3-dimensional parametric function. Preferably, this is accomplished using shaders in the GPU. Finally, a 3-dimensional raster function on the GPU is used to 3-dimensionally raster the weighted geometrical lines to a 3-dimensional texture.

BRIEF DESCRIPTION OF THE FIGURES

The present invention together with its objectives and advantages will be understood by reading the following description in conjunction with the drawings, in which.

DETAILED DESCRIPTION OF THE INVENTION

The present invention provides a method of reconstructing a tomographic image using a GPU. The method includes the steps of forward-projecting the tomographic image along a list of geometrical lines using a GPU, back projecting the list of geometrical lines into a 3-dimensional volume using the GPU, utilizing results of the forward-projecting and back-projecting to reconstruct the tomographic image, and providing the reconstructed tomographic image as an output.

In imaging systems, blurring occurs due to several physical effects (for example, scatter can deflect photons, detectors are not perfect, there is electronic noise). This creates an uncertainty as to the exact line from which the photon was emitted. In the absence of such uncertainty, the response of the system is a perfect, infinitely thin line. Modeling the uncertainty improves the performance of the algorithm. This modeling is done using broad distributions that simulate the uncertainty in the back- and forward-projection. In a preferred embodiment, this modeling is implemented using a parametric 3-dimensional blurring kernel. In one embodiment, the parametric 3-dimensional blurring kernel is a 2-dimensional gaussian perpendicular to each line. In another embodiment, the blurring kernel is a 1-dimensional time of flight blurring kernel. In yet another embodiment, the blurring kernel uses trilinear interpolation. Examples of projection techniques using these models include, but are not limited to, the tri-linear interpolation technique and the Gaussian tube of response (TOR) technique. In the GPU, these methods are implemented using shader programs. For the back-projection, the blurring kernel is programmed in the pixel shader and a thick line is used to raster to a large area. For the forward-projection, the blurring kernel is implemented in a shader as part of the texture look-up.

Preferably, the GPU is initialized prior to implementing the method of the present invention. This initializing preferably includes the steps of setting projection to be orthographic, activating blending, and setting the target of rastering to be a 2-dimensional texture map.

The present invention provides methods of forward-projecting a tomographic image along a list of geometrical lines using a GPU. Forward projection can be mathematically defined as:

$$\sum_{j=1}^{J} P_{ij} \lambda_j$$

where $\lambda$ is the voxel space, indexed by $j=1, \ldots, J$, i refers to the index of the line inside the list, and $P_{ij}$ represents how much line i contributes to voxel j. Each geometrical line connects two detectors, in the case of positron emission tomography (PET), or a radiation source and a detector, in the case of single photon emission computed tomography (SPECT) or X-Ray computed tomography (X-Ray CT). The same geometrical line can be repeated within a list of lines. Alternatively, the list may be a list of weighted lines derived from a sinogram, a histogram, or a timogram acquired from a tomographic scanner.

Figure 1:
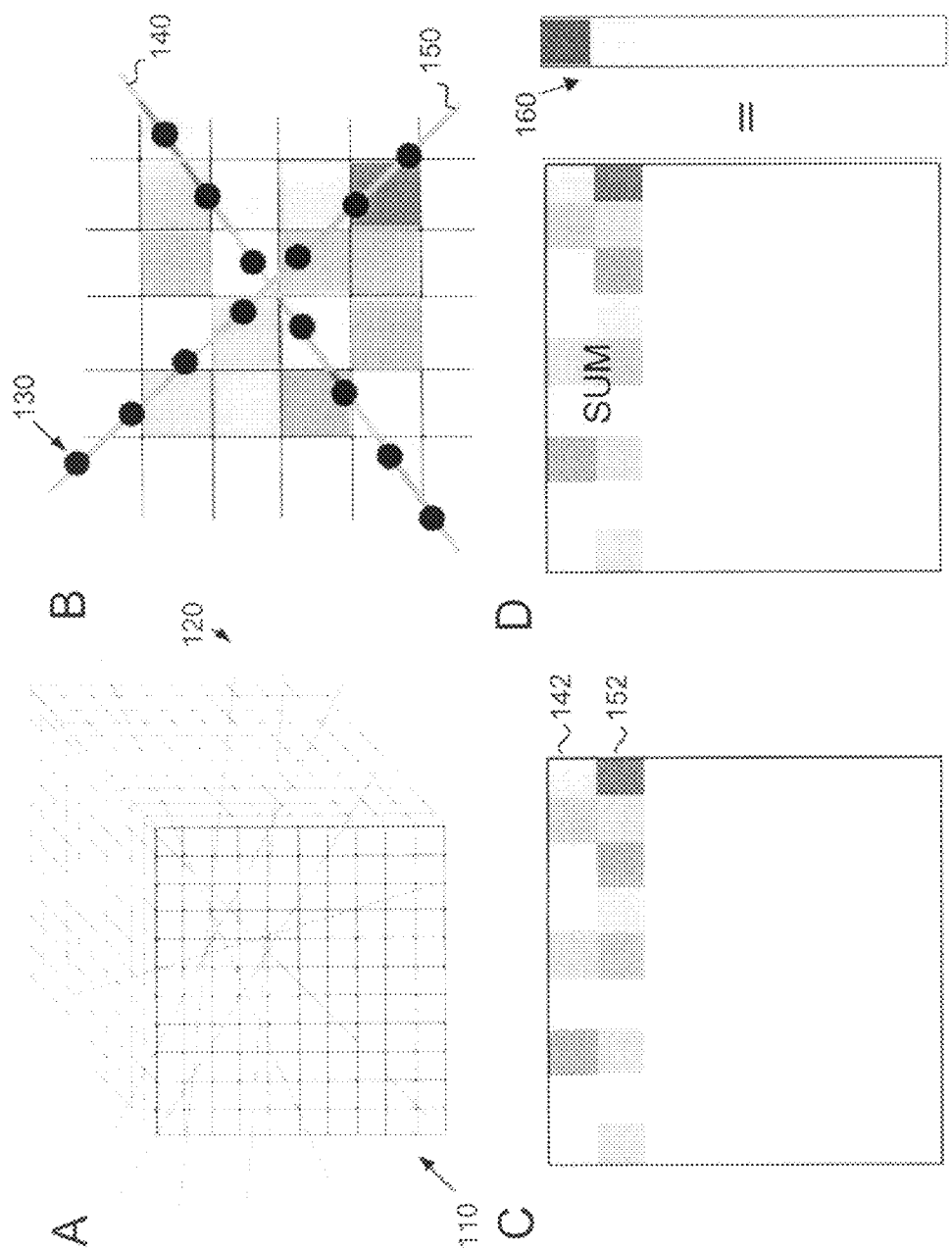
FIG. 1 shows a schematic of forward-projection according to the present invention

FIG. 1 shows a schematic representation of a forward projection algorithm implemented on a GPU according to the present invention. In a first step (FIG. 1A), a 3-dimensional voxel array 110 is inputted into a GPU. The voxel array models a tomographic image. In addition to the voxel array, a list of geometrical lines 120 (that can be events recorded by the system, or lines representing histogram bins, or X ray line projections) taken from the set of lines of response of the scanner are also inputted. In a preferred embodiment, a subset of the event list is read from a CPU and loaded into the GPU's 32-bit floating-point texture memory. This texture contains the coordinates of the line end-points as well as the value of each line. Different color channels, such as RGBA (red-green-blue-alpha), provided by the GPU may be used to store each of the endpoints.

In FIG. 1B, lines 140 and 150 are pictured as going through the 3-dimensional array. The difference in grayscale shading represents different values for the voxels. The weighted sum of voxel values is determined at several sample points 130 along each geometrical line. In one embodiment, this is accomplished using shaders in the GPU. The shader looks-up voxel values surrounding the sample points on the geometrical line. A resolution blurring kernel can be used to determine the value of the sample.

Next, the weighted samples values of the voxels along each of the geometrical lines are recorded into GPU memory. In one embodiment, shown in FIG. 1C, the weighted samples values along the geometrical lines 140 and 150 are mapped onto sequential parallel lines 142 and 152, respectively. The original 3-dimensional geometrical lines 140 and 150 have different lengths, but the texture mapping function of the GPU stretches the texture so it fills in the whole destination 2-dimensional line 142 and 152. This is a property of texture mapping.

Finally, the numerical integral (i.e. the sum) of the weighted samples values of the voxels along each of the geometrical lines is calculated in the GPU. In a preferred embodiment, the sum is computed along each sequential parallel line using a pixel shader in the GPU (FIG. 1D). This shader draws a vertical line 160 in which the output value results from the sum over all the voxels over each sequential parallel line. The result is the forward projection of the tomographic image along each geometrical line. The output may then be sent to a CPU.

The present invention also provides methods of back-projecting a list of geometrical lines into a 3-dimensional volume using a GPU. Given a list of N lines indexed by i, and a set of values $V_i$ (one value for each line), the back-projection of all the $V_i$ along all the lines onto a voxel j can be written as:

$$\sum_{i=1}^{N} (P_{ij} * V_i)$$

Figure 2:
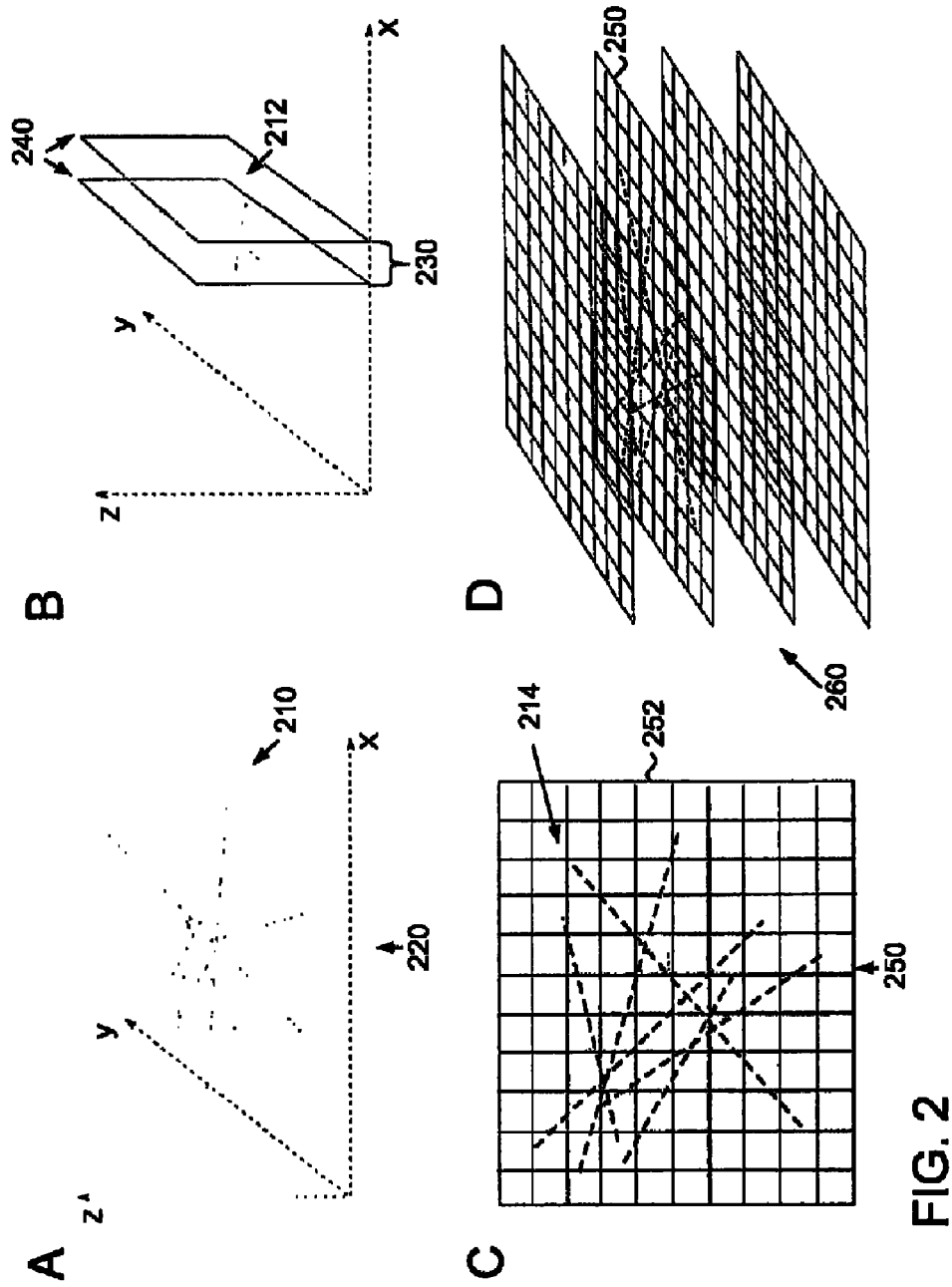
FIG. 2 shows a schematic of back-projection according to the present invention.

FIG. 2 shows a schematic representation of a back projection algorithm implemented on a GPU according to the present invention. In a first step, a list of geometrical lines is inputted into a GPU. The geometrical lines may be list-mode event data acquired from any type of tomographic scanner, including but not limited to a PET scanner, a SPECT scanner, or an X-Ray CT scanner. Alternatively, the geometrical lines may be a list of weighted lines derived from a sinogram, histogram, or timogram. Preferably, the geometrical lines are defined in the GPU as a set of geometrical 3-dimensional lines 210, which are contained inside a 3-dimensional volume 220 that is defined by the scanner geometry and/or the user (FIG. 2A). Next, a slice 230 is defined in 3-dimensional volume 220. This may be accomplished, e.g., by configuring the GPU to set cutting planes 240 through the 3-dimensional volume (FIG. 2B). In one embodiment, the cutting planes define slices that are one pixel deep. In other embodiments, the cutting planes define slices that are either four or a multiple of four pixels deep, e.g. 8, 12, 16, etc. Preferably, the cutting planes are set to comprise 4 slices and color is used to encode slice depth. Encoding the depth of the slices with color allows the use of all the shaders in the GPU, where most of the computational power is concentrated. In the next step, a 2-dimensional texture 250 of each of the slices is defined by projecting and rastering the portions of geometrical lines 212 that are within the slice 230 (indicated by dashed lines 214) into a set of weighted pixels, such as pixel 252 (FIG. 2C). In one embodiment, projecting is accomplished using a vertex shader. The vertex shader applies an orthographic projection to the 3-dimensional line endpoints and outputs the 2-dimensional line endpoints. Preferably, for each line 214, the value of a rastered pixel along the line is defined by the product of the value of the line (for example the number of events that occurred along the line) and the blurring kernel used. This operation is done using the pixel shader. The pixel values are then accumulated using blending for each line that intersects the pixel (values are indicated in FIG. 2C and FIG. 2D by grayscale level, with darker pixels equivalent to larger numbers). In another embodiment, the process described in FIG. 2C is accomplished using a draw all lines operation in the GPU. Preferably, the 2-dimensional texture is copied to another accumulation texture regularly (approximately every 20,000 lines) to maximize dynamic range and avoid overflow and underflow. Each 2-dimensional texture 250 is then inserted into a 3-dimensional voxel array 260 (FIG. 2D) stored on the GPU. Preferably, 3-dimensional voxel array 260 is stored within texture memory of the GPU. This process is then repeated by cutting additional slices through the geometrical volume and repeating steps C and D.

A method of back-projecting tomographic data using a 4 pixels-deep slicing method is described as follows. First, a 1×4 pixels texture is created. This texture is not changed during the execution of the program. The method of initializing the texture is as follows: The first pixel is assigned the color RED (1, 0, 0, 0). The second is assigned the color GREEN (0,1,0,0). The third is assigned the color BLUE (0,0,1,0). The fourth is assigned the arbitrary color ALPHA (0,0,0,1). The ALPHA is not a real color, but it does not matter for this purpose. Next, the cutting planes are set such that the slice is 4 pixels deep. The 1×4 texture is then mapped onto each line such that the first pixel of the texture (RED) gets mapped onto the intersection of the line and the first cutting plane and the $4^{th}$ pixel of the texture (ALPHA) gets mapped onto the intersection of the line and the second cutting plane. Next, the lines are drawn. Because each line has its texture, its color is going to go from red to green to blue to alpha. This means that the information will be first written in the RED channel, then in the GREEN channel, then BLUE and then ALPHA. Thus, spatial encoding is done through color texture mapping. This leads to a 4× increase in speed because the lines are drawn into 4 planes at a time.

A 16-pixels deep slicing method uses a new GPU extension called MRT (Multiple Rendering Target) that allows the user to render to 4 textures at a time. 4 Textures*4 color channels means 16 planes can be drawn to simultaneously. The only variation is that the 4×1 texture used above needs to be a 16×1 texture.

In an alternative embodiment, the list of geometrical lines may be back-projected as follows. First, a list of geometrical lines is inputted into the GPU. Next, the geometrical lines are weighted using a 3-dimensional parametric function. Finally, a 3-dimensional raster function on the GPU is used to 3-dimensionally raster the geometrical lines directly to a 3-dimensional texture.

The inventive forward- and back-projection methods may be used in the context of any list-mode image reconstruction algorithm. Preferably, the forward- and back-projection algorithms are used in the context of an iterative algorithm, such as an expectation maximization algorithm or a maximum a posteriori (MAP) method. A preferred expectation maximization algorithm is the 3D list-mode Ordered-Subset Expectation Maximization (3D List-mode OSEM) algorithm. The forward- and back-projection algorithms may also be used in the context of sinogram, histogram, or timogram-based image reconstruction algorithms, by converting the sinogram, histogram or timogram bins into weighed lines.

The forward- and back-projection algorithms may be executed on any GPU, including but not limited to those made by ATI and Nvidia. The GPU may be programmed using, for example, OpenGL, Direct X, HLSL, and/or Cg.

EXAMPLES

To test the method of the present invention, images were reconstructed using a list-mode 3D-OESM algorithm implemented on a GPU. This algorithm is an iterative algorithm that uses both the line back-projection and forward-projection operators described above. List-mode is OSEM can be represented mathematically by the following formula:

$$\lambda_j^{m,l} = \underbrace{\frac{\lambda_j^{m,l-1}}{\sum_{i=1}^{I} w_{ii} p_{ij}}}_{C} \left[ \underbrace{\sum_{k \in S_l} p_{i,j}}_{B} \underbrace{\frac{1}{\sum_{ji=1}^{J} p_{i_k b} \lambda_j^{Hl,l-1}}}_{A} \right]$$

where A is the forward projection, B is the back-projection of the inverse of A, and C is the normalization.

List-mode 3D-OSEM iteratively improves a sequence of image estimates until it converges to the best image of the object scanned by the medical device, and incorporates the following steps:
1. Load a subset of event lines.
2. Forward project the 3D voxel array along these lines. For each line, this results in a positive real number Vk.
3. Prepare a new blank 3D voxel array.
4. Back-project all the lines, weighting each line by 1/Vk, into the blank 3D voxel array.
5. For each voxel of the new voxel array, multiply by the old voxel array and divide by a normalization factor that is computed beforehand.
6. The new 3D voxel array is the new (better) estimate for the image volume.
7. Repeat steps 2-5 to obtain a reconstructed tomographic image.

1-mm Resolution Pre-Clinical PET System

To test our implementation of list-mode 3D-OSEM, we first worked on reconstruction of simulated data. Data was first generated using the Monte-Carlo package GATE by simulating a pre-clinical PET system currently under development. This system has 1-mm resolution Cadmium-Zinc-Telluride (CZT) detectors arranged in a 8*8*8 cm³ box geometry. Coincident events can be recorded along more than 8 billion LORs, which dictates the use of list-mode image reconstruction algorithms. In addition to that, the SRM is gigantic and would be impossible to store even on a computer cluster. For this reason, on-the fly computation of the coefficients is required for practical implementation.

Figure 3:
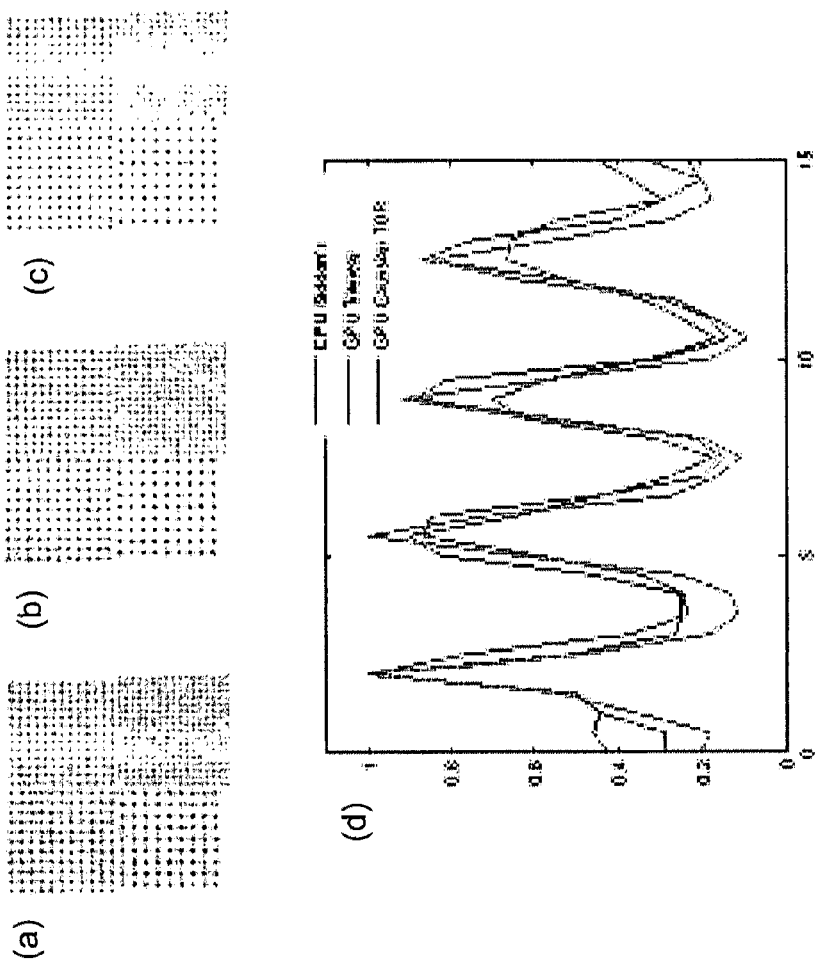
FIG. 3 compares reconstructions of resolution phantoms using a CPU versus using a GPU according to the present invention.

25 million counts were recorded from a phantom consisting of spheres of different sizes (1 mm, 1.25, 1.5, 1.75) placed in a single plane, separated by twice the diameter. Data was reconstructed on a single CPU using a version of list-mode 3DOSEM that uses Siddon's algorithm as projector (FIG. 3(a)). Reconstruction was also done on the GPU using list-mode 3D-OSEM and two different projection methods: tri-linear interpolation (FIG. 3(b)) and Gaussian TOR (FIG. 3(c)). The FWHM for the Gaussian TOR was chosen to be 1 mm, a value equal to the crystal width. For the trilinear interpolation method, the voxel size (0.5 mm) allowed the width of the triangular kernel to be 1 mm also. 20 image updates with 1.5 m events per subsets were done for Siddon and tri-linear interpolation. 30 image updates were applied for Gaussian TOR. The Gaussian kernel works as a low-pass filter and allows in general the running of more updates. We found that the reconstructed resolution was not degraded by our implementation of list-mode 3D-OSEM on the GPU. In addition, it was possible to run more iterations when using the Gaussian TOR method since it better filters the image noise. This allowed us to get the higher contrast observed on the profile (FIG. 3(d)) while keeping the noise low. The profile shown in FIG. 3(d) is through four 1.75 mm spheres.

Vista DR Pre-Clinical PET System

The Vista DR (previously named Argus) is a pre-clinical PET scanner with two depth-of-interaction layers of 1.55 mm pitch crystals. The depth identification is done by pulse shape discrimination. The useful field-of-view is 6.7 cm transversely and 4.6 cm axially. 6,084 crystal elements provide 28.8 million LORs, allowing for histogram-mode reconstruction. Acquisition is fully 3D. We performed two phantom studies (hot rod and cold rod phantoms) and a small-animal study to evaluate the performance of the GPU reconstruction. Data was generated and then reconstructed using the following algorithms: standard FORE+2D-OSEM (provided with the scanner), CPU-based listmode 3D-OSEM (Siddon's), GPU-based histogram-mode 3DOSEM (Tri-linear and Gaussian TOR).

The hot rod phantom (Micro Deluxe phantom, Data Spectrum) was filled with 110 µCi of 18 F and imaged for 20 minutes. The rods diameters were 1.2, 1.6, 2.4, 3.2, 4.0 and 4.8 mm. The spacing between the centers was twice the diameter. Data was collected in histogram mode. OSEM subsets were formed using a random partition of the LORs.

Figure 4:
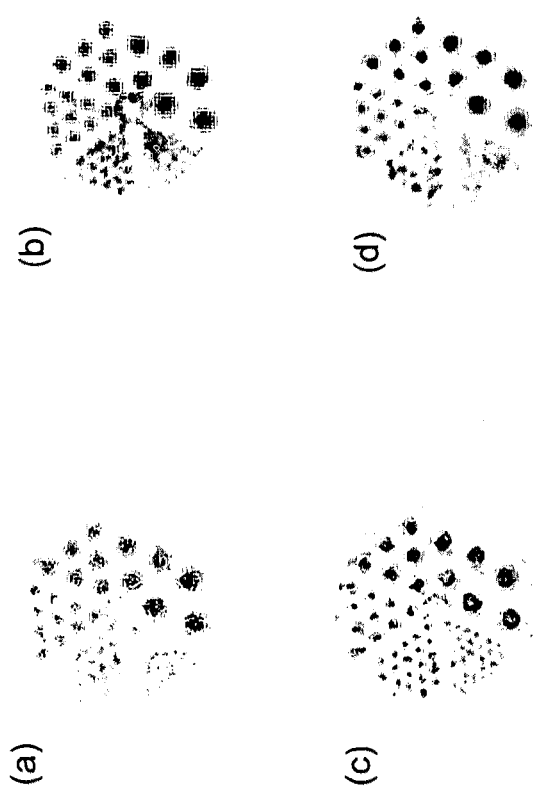
FIG. 4 compares reconstructions of hot rod phantoms using a CPU versus using a GPU according to the present invention.

Simple 3D-OSEM based on CPU and the Siddon's projector did not produce very high quality images for the Vista DR system despite using 10× dithering to increase sampling (FIG. 4(a)). This is largely caused by the substantial difference between the line-integral model and the real detector response of the system. Similarly, the tri-linear interpolation technique, despite providing better images than Siddon, did not make it possible to resolve the 1.2 mm rods (FIG. 4(b)). In contrast, the Gaussian TOR technique was able to resolve all the rods (FIG. 4(c)). We used a 1.4 mm FWHM TOR (slightly smaller than the 1.55 mm crystal pitch). FORE+2D-OSEM is also shown in FIG. 4(d). The number of image updates for each image is 40 for (a), 60 for (b), 12*8 for (c) and 2*32 for (d).

Figure 5:
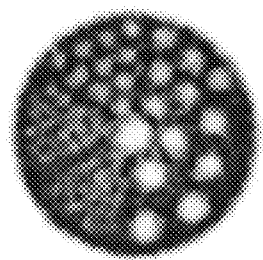
FIG. 5 compares reconstructions of cold rod phantoms using a CPU versus using a GPU according to the present invention.
Figure 5:
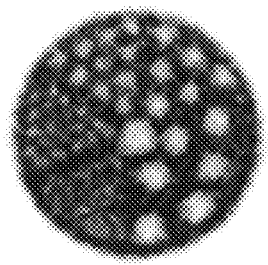

The cold rod phantom (Micro Deluxe phantom, Data Spectrum) was filled with 200 µCi of $^{18}$F and imaged for 20 minutes. The rod diameters were 1.2, 1.6, 2.4, 3.2, 4.0 and 4.8 mm. The spacing between the centers was twice the diameter. Reconstruction was done with GPU-based 3D-OSEM with Gaussian TOR projection (FIG. 5(a)) and FORE+2D-OSEM (FIG. 5(b)). 12*8 updates were run for (a) and 2*32 for (b). It is not clear whether Gaussian TOR outperforms FORE+2D-OSEM in term of resolution for the cold rod phantom. However, the images produced have better uniformity. In addition, the ability to reconstruct cold lesions is clearly demonstrated.

Figure 6:
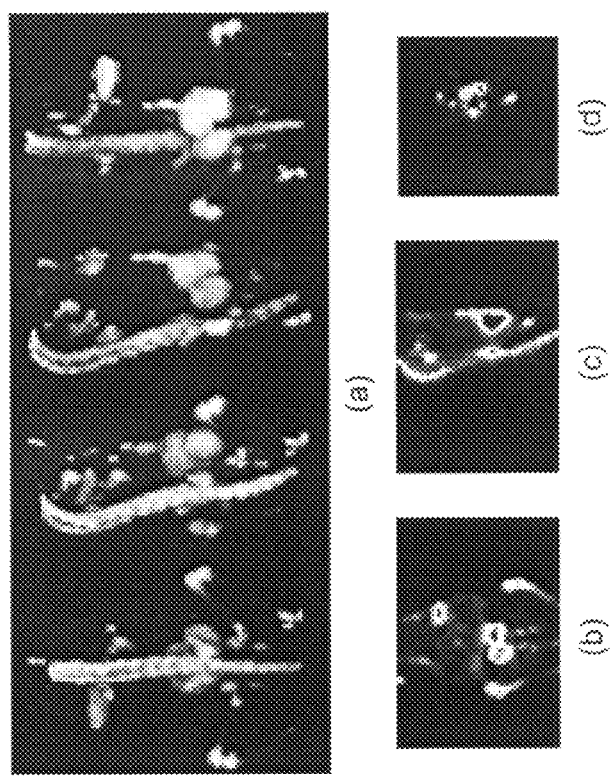
FIG. 6 shows an image of a nude mouse implanted with an osteosarcoma in the belly that was reconstructed using a GPU according to the present invention.

In another study, we looked at data acquired from a mouse cancer model. An osteosarcoma xenograft was implanted in the belly of a nude mouse just above the bladder. An injection of 100 µCi of Na—$^{18}$F was performed on the mouse. After 1 h30 uptake, the mouse was imaged on the Vista DR for 1 hour. Images were reconstructed with the GPU-based 3D-OSEM using the Gaussian TOR. 12 iterations of the algorithm were run using 8 subsets, resulting in 96 effective image updates. FIG. 6 shows a volumetric rendering of the mouse under different angles (a), as well as saggital (b), coronal (c), and transverse (d) slices through the volume.

Processing Time

The processing time for each reconstruction method was measured. CPU-based 3D-OSEM was benchmarked on an AMD Athlon 64 3500+ (2.2 GHz). The GPU used for the same task was the NVIDIA GeForce 7900GTX GPU. The values shown in Table I were measured for 2 iterations of OSEM. Histogram-mode was used for 3D-OSEM. The measured time includes both the Fourier rebinning and the 2D-OSEM for FORE+2D-OSEM. Note that depending on the projection method that is used, different numbers of image iterations can be run to achieve the best image.

As a reference, the histogram-mode 3D-OSEM software FIRST takes, for two iterations, 3876 seconds on a single AMD Opteron 244 (1.8 GHz) and 5232 seconds on a single Intel Xeon EMT64 (2.8 GHz). This version of 3D-OSEM stores a Monte-Carlo generated SRM as a look-up table in memory. The compressed coefficients of the SRM are extracted on-the-fly.

TABLE I

| Algorithm | Reconstruction time |
| --- | --- |
| CPU 3D-OSEM (Siddon) | 5,510 s |
| CPU 3D-OSEM (Siddon + 10X dither.) | 55,100 s |
| GPU 3D-OSEM (Trilinear interp.) | 125 s |
| GPU 3D-OSEM (Gaussian TOR) | 340 s |
| CPU FORE + 2D-OSEM | 120 s |

As one of ordinary skill in the art will appreciate, various changes, substitutions, and alterations could be made or otherwise implemented without departing from the principles of the present invention. Accordingly, the scope of the invention should be determined by the following claims and their legal equivalents.

What is claimed is:

1. A method of reconstructing a tomographic image, comprising:
   a) forward-projecting said tomographic image along a list of individual geometrical lines using a graphics processing unit (GPU), wherein said individual geometrical lines comprise list-mode event data or a list of weighted lines, and wherein said forward-projecting comprises multiple independent forward projections of said tomographic image onto individual lines;
   wherein said forward-projecting further comprises:
      i) inputting into said GPU a 3-dimensional voxel array;
      ii) inputting said list of individual geometrical lines into said GPU, wherein said list of individual geometrical lines is defined within said 3-dimensional voxel array;
      iii) determining weighted samples values by sampling said 3-dimensional voxel array at several locations along each of said individual geometrical lines in said GPU;
      iv) recording said weighted samples values of said voxels along each of said individual geometrical lines into GPU memory, where said weighted samples are recorded into GPU memory using texture mapping of said weighted samples;
   b) back-projecting said list of individual geometrical lines into a 3-dimensional volume using said GPU, wherein said back projecting comprises multiple independent back projections of said individual lines onto said 3-dimensional volume;
   c) utilizing results of said forward-projecting and said back projecting to reconstruct said tomographic image; and
   d) providing said reconstructed tomographic image as an output.

2. The method as set forth in claim 1, wherein said forward-projecting, said back-projecting, or said forward-projecting and said back-projecting is implemented using a parametric 3-dimensional blurring kernel.

3. The method as set forth in claim 2, wherein said parametric 3-dimensional blurring kernel is a 2-dimensional Gaussian perpendicular to each of said lines.

4. The method as set forth in claim 2, wherein said parametric 3-dimensional blurring kernel uses trilinear interpolation.

5. The method as set forth in claim 2, wherein said parametric 3-dimensional blurring kernel is a 1-dimensional time of flight blurring kernel.

6. The method as set forth in claim 1, wherein said forward-projecting further comprises:
   calculating a sum of said weighted samples values for each of said individual geometrical lines in said GPU memory.

7. The method as set forth in claim 6, wherein said calculating comprises using shaders in said GPU.

8. The method as set forth in claim 6, wherein said determining weighted sample values comprises using shaders in said GPU.

9. The method as set forth in claim 6, where said weighted samples are recorded onto sequential parallel lines.

10. The method as set forth in claim 1, wherein said back-projecting comprises:
    a) inputting into said GPU said list of individual geometrical lines;
    b) defining slices in a 3-dimensional volume, wherein said 3-dimensional volume comprises said individual geometrical lines;
    c) defining a 2-dimensional texture of each of said slices by projecting and rastering the portion of said individual geometrical lines that is contained within each of said slices into a set of weighted pixels;
    d) inserting each of said 2-dimensional textures into a 3-dimensional voxel array stored on said GPU.

11. The method as set forth in claim 10, wherein said slices in said 3-dimensional volume are defined using a cutting planes operation on said GPU.

12. The method as set forth in claim 11, wherein said cutting planes are set to comprise 4 slices and wherein color is used to encode slice depth.

13. The method as set forth in claim 10, wherein said projecting is accomplished using shaders in said GPU.

14. The method as set forth in claim 1, wherein said back-projecting comprises:
    a) inputting into said GPU said list of individual geometrical lines;
    b) weighting said individual geometrical lines using a 3-dimensional parametric function; and
    c) using a 3-dimensional raster function on said GPU to 3-dimensionally raster said weighted individual geometrical lines to a 3-dimensional texture.

15. The method as set forth in claim 14, wherein said weighting is accomplished using shaders in said GPU.

16. The method as set forth in claim 1, further comprising initializing said GPU.

17. The method as set forth in claim 16, wherein said initializing comprises the steps of:
    a) setting projection to be orthographic;
    b) activating blending; and
    c) setting the target of rastering to be a 2-dimensional texture map.

18. The method as set forth in claim 1, wherein said list-mode event data is acquired from a tomographic scanner, and said list of weighted lines is derived from a sinogram, a histogram or a timogram acquired from a tomographic scanner.

19. The method as set forth in claim 18, wherein said tomographic scanner is selected from the group consisting of a PET scanner, a SPECT scanner, and an X-Ray CT scanner.

20. The method as set forth in claim 18, wherein said list-mode event data contains time-of-flight information or temporal information.

* * * * *